United States Patent
Mills

(10) Patent No.: US 10,179,223 B2
(45) Date of Patent: Jan. 15, 2019

(54) APPARATUS AND METHODS FOR INDUCING SLEEP

(71) Applicant: BRAINTRAIN2020 LIMITED, Sheffield (GB)

(72) Inventor: Richard Mills, Sheffield (GB)

(73) Assignee: Braintrain2020 Limited, Sheffield (GB)

( * ) Notice: Subject to any disclaimer, the term of this patent is extended or adjusted under 35 U.S.C. 154(b) by 408 days.

(21) Appl. No.: 15/022,792

(22) PCT Filed: Sep. 16, 2014

(86) PCT No.: PCT/GB2014/052798
§ 371 (c)(1),
(2) Date: Mar. 17, 2016

(87) PCT Pub. No.: WO2015/040373
PCT Pub. Date: Mar. 26, 2015

(65) Prior Publication Data
US 2016/0228674 A1 Aug. 11, 2016

(30) Foreign Application Priority Data
Sep. 20, 2013 (GB) .................................. 1316735.8

(51) Int. Cl.
*A61M 21/02* (2006.01)
*A61M 21/00* (2006.01)
*A61N 5/06* (2006.01)

(52) U.S. Cl.
CPC ....... *A61M 21/02* (2013.01); *A61M 2021/005* (2013.01); *A61M 2021/0027* (2013.01);
(Continued)

(58) Field of Classification Search
CPC .......................................... A61M 21/00–21/02
See application file for complete search history.

(56) References Cited

U.S. PATENT DOCUMENTS 4,702,475 A * 10/1987 Elstein ............... A63B 69/0053
273/445
5,036,858 A 8/1991 Carter et al.
(Continued)

FOREIGN PATENT DOCUMENTS

DE 19905145 A1 8/2000
WO WO2007/105127 A1 9/2007

OTHER PUBLICATIONS

Nightwave; NightWave sleep assistant (product information); 5 pgs.; retrieved from the internet: (http://web.archive.org/web/20121227005517/http://www.nightwave.co.uk/index.htm); print/retrieval date: Jun. 9, 2016.

*Primary Examiner* — Thaddeus B Cox
(74) *Attorney, Agent, or Firm* — Shay Glenn LLP

(57) ABSTRACT

Apparatus for inducing sleep comprising: a. a display for providing a subject with a light stimulus; b. a base unit on which said display is mounted such that the display is selectively positionable, in use, into a field of view of a subject; c. input means for recording an active input provided by the subject in response to the stimulus; d. processing means for processing said active input to determine a characteristic of said active input; and e. a base unit housing one or more of said means, wherein the apparatus is capable of sequentially providing the subject with a plurality of stimuli, each next stimulus being based on a characteristic determined from the active input made in response to a previous stimulus, and wherein a position and/or brightness and/or a color and/or a shape of the next stimulus on the display and/or a time interval between stimuli is based on the characteristic of the active input provided in response to a previous stimulus.

23 Claims, 2 Drawing Sheets

(52) U.S. Cl.
CPC ............... *A61M 2021/0044* (2013.01); *A61M 2205/3303* (2013.01); *A61M 2205/3306* (2013.01); *A61M 2205/3368* (2013.01); *A61M 2205/3375* (2013.01); *A61M 2205/502* (2013.01); *A61M 2230/06* (2013.01); *A61M 2230/10* (2013.01); *A61M 2230/30* (2013.01); *A61M 2230/42* (2013.01); *A61M 2230/50* (2013.01); *A61N 2005/0648* (2013.01)

(56) References Cited

U.S. PATENT DOCUMENTS

| | | | |
|---|---|---|---|
| 5,092,669 A | 3/1992 | Anderson | |
| 5,219,322 A | 6/1993 | Weathers | |
| 5,259,390 A | 11/1993 | Maclean | |
| 5,619,291 A * | 4/1997 | Putnam | A61B 5/16 351/239 |
| 9,601,026 B1 * | 3/2017 | Merzenich | A63F 13/80 |
| 2009/0062598 A1 * | 3/2009 | Haisma | A61M 21/00 600/28 |
| 2011/0310613 A1 * | 12/2011 | Evans | A61M 21/02 362/272 |
| 2015/0025301 A1 * | 1/2015 | Rosenzweig | A61M 21/02 600/27 |

* cited by examiner

APPARATUS AND METHODS FOR INDUCING SLEEP

TECHNICAL FIELD

This invention relates to the field of apparatus and methods for inducing sleep.

BACKGROUND

Sleep disorders, including difficulties in either falling asleep or remaining asleep, are increasingly common; one in three adults in the UK are reported to suffer from a sleep disorder of some kind. A lack of sleep can result in impaired concentration and reaction times whilst awake, as well as a general feeling of tiredness. Difficulties in falling asleep can be caused by an inability to ignore conscious thoughts, which may be caused by stress or anxiety.

Severe sleep disorders may be treated using drugs that promote sleep. Although such treatment can be effective for a short time, the drugs typically have undesirable side effects and may be addictive. For this reason many drugs used to improve sleep are approved for short-term use only. Natural herbal therapies for helping a subject to fall asleep are also available. However, whilst these therapies do not usually cause the undesirable side effects associated with other drug based therapies, they are also typically less effective.

Alternative approaches for inducing sleep include meditative approaches in which a stimulus is provided to encourage the subject to relax, for example by providing a light whose intensity varies cyclically so that the subject may match the frequency of their breathing to frequency of the cycles of the light. In this way the frequency of the cycles of the light may be gradually reduced so that the subject is encouraged to slow their breathing at a predetermined rate. An example of such an approach is that implemented by the Nightwave sleep assistant (http://wwww.nightwave.co.uk/index.htm).

Such approaches have the advantage that they have very limited side effects. However, they have the disadvantage that they do not engage with or adapt to the subject, so they may be ineffective for certain individuals or on occasions when the subject finds it particularly difficult to get to sleep.

Another approach to improving sleep involves taking physiological measurements from the subject and attempting to manipulate their surrounding environment to improve sleep. Although such approaches may help the subject to sleep better once they have fallen asleep, they are of limited usefulness in inducing the subject to fall asleep in the first instance.

Embodiments of the present invention aim to provide apparatus and methods for inducing sleep which at least partially mitigate the problems described above.

BRIEF SUMMARY OF THE DISCLOSURE

According to a first aspect of the invention there is provided apparatus for inducing sleep comprising:
  a. stimulus means for providing a subject with a stimulus;
  b. input means for recording an active input provided by the subject in response to the stimulus;
  c. processing means for processing said active input to determine a characteristic of said active input; and
  d. a base unit housing one or more of said means,
wherein the apparatus is capable of sequentially providing the subject with a plurality of stimuli, each next stimulus being based on a characteristic determined from the active input made in response to a previous stimulus.

In an embodiment, the stimulus means is a display and said stimulus is light. The display can be mounted on said base unit and selectively positionable, in use, into a field of view of a subject.

Preferably, a position and/or brightness and/or a colour and/or a shape of the next stimulus on the display and/or the time interval between stimuli is based on the characteristic of the active input provided in response to a previous stimulus. As the subject becomes less alert, the delay time between individual light stimuli could be increased. Eventually, as the subject ceases to respond actively to the apparatus, no further light stimuli are provided and the apparatus may switch itself off.

In an embodiment, the display comprises an upper display and a lower display. The upper display and/or said lower display may each comprise an elongate track, preferably oriented generally horizontally when in the field of view of a subject. Each elongate track may be mounted on a support arm attached to said base unit, each elongate track being vertically separated from the other.

In an embodiment, said processing means determines whether said next stimulus should be displayed on the upper or the lower display depending on said characteristic of said active input. Preferably, at least the first of said stimuli is displayed on said upper display.

In an embodiment, said stimuli comprise a sequence of lights moving horizontally from left to right across the subject's field of view.

In an alternative embodiment, said stimulus means is an audio transducer and said stimulus is sound. The audio transducer may be, for example, a loudspeaker, headphones or earphones. Preferably, a volume and/or pitch and/or timbre of the next sound stimulus and/or the delay time between sound stimuli is based on the characteristic of the active input provided in response to a previous sound stimulus.

For example, the volume and pitch may be decreased as the subject becomes less alert, or the timbre changed to a softer sound. As the subject becomes less alert, the delay time between individual sound stimuli could be increased. Eventually, as the subject ceases to respond actively to the apparatus, no further sound stimuli are provided and the apparatus may switch itself off.

In an embodiment, said active input comprises the actuation of a switch, for example the pressing of a button. The characteristic of said active input may comprise a time delay between the provision of the stimulus to the subject and the actuation of the switch by the subject.

In an embodiment, the display of said next stimulus transitions from said upper display to said lower display in response to an increase in said time delay.

The apparatus may further comprise monitoring means for recording a physiological characteristic of the subject, wherein said next stimulus is based on characteristic of said active input and said physiological characteristic. The physiological characteristic may be, for example, one or more of the subject's heart rate, electrical brain activity, body temperature, blood pressure and respiratory rate.

The apparatus may further comprise ambient monitoring means for recording an ambient characteristic of the subject's environment, wherein said next stimulus is based on characteristic of said active input and said ambient characteristic. The ambient characteristic may be one or more of, for example, time, temperature, light level and sound level.

In an embodiment, the determination of said next stimulus is additionally based on a characteristic of at least one active input provided in response to a stimulus provided before the immediately preceding stimulus.

According to another aspect of the invention, there is provided apparatus for inducing sleep comprising:
a. a display for providing a subject with a light stimulus;
b. a base unit on which said display is mounted such that the display is selectively positionable, in use, into a field of view of a subject;
c. input means for recording an active input provided by the subject in response to the stimulus;
d. processing means for processing said active input to determine a characteristic of said active input; and
e. a base unit housing one or more of said means, wherein the apparatus is capable of sequentially providing the subject with a plurality of stimuli, each next stimulus being based on a characteristic determined from the active input made in response to a previous stimulus, and wherein a position and/or brightness and/or a colour and/or a shape of the next stimulus on the display and/or a time interval between stimuli is based on the characteristic of the active input provided in response to a previous stimulus.

According to another aspect of the invention there is provided a method for inducing sleep comprising the steps of:
a. providing a subject with an initial stimulus;
b. recording an active input provided by the subject in response to the initial stimulus;
c. processing said active input to determine a characteristic of said input;
d. providing the subject with a further stimulus based on said characteristic;
e. recording a further active input provided by the subject in response to the further stimulus;
f. processing the further active input provided by the subject in response to the second stimulus to determine a further characteristic; and
g. sequentially providing the subject with a plurality of further stimuli, each further stimulus being based on a characteristic determined from the active input made in response to the previous stimulus.

The method can be performed using the apparatus of any of the preceding paragraphs.

Within the scope of this application it is expressly intended that the various aspects, embodiments, examples and alternatives set out in the preceding paragraphs, in the claims and/or in the following description and drawings, and in particular the individual features thereof, may be taken independently or in any combination. Features described in connection with one embodiment are applicable to all embodiments, unless such features are incompatible.

BRIEF DESCRIPTION OF THE DRAWINGS

One or more embodiments of the invention will now be described, by way of example only, with reference to the accompanying drawings, in which.

DETAILED DESCRIPTION

A subject consciously thinking about problems and worries may find it difficult to fall asleep. The apparatus and methods of the invention create a distraction for the conscious mind to help the subject rest and relax, inducing sleep more successfully. The apparatus and methods of the invention encourage and use distraction techniques such as meditation and trigger based cognitive therapy to help the subject unwind and fall asleep.

Cognitive therapy helps create new neural pathways through habit-forming patterns using anchors/triggers. After repeated use, the mere switching on of the apparatus of the present invention when the subject goes to bed may be enough of an anchor in itself to instruct the mind to relax. Operation of the apparatus as described below provides patterns of stimuli to the subject to distract them from conscious thoughts and worries which might otherwise deter them from falling asleep, thus reducing the time taken to induce sleep. The stimuli are tailored to the subject by responding to active input by the subject, as described below.

Figure 1:
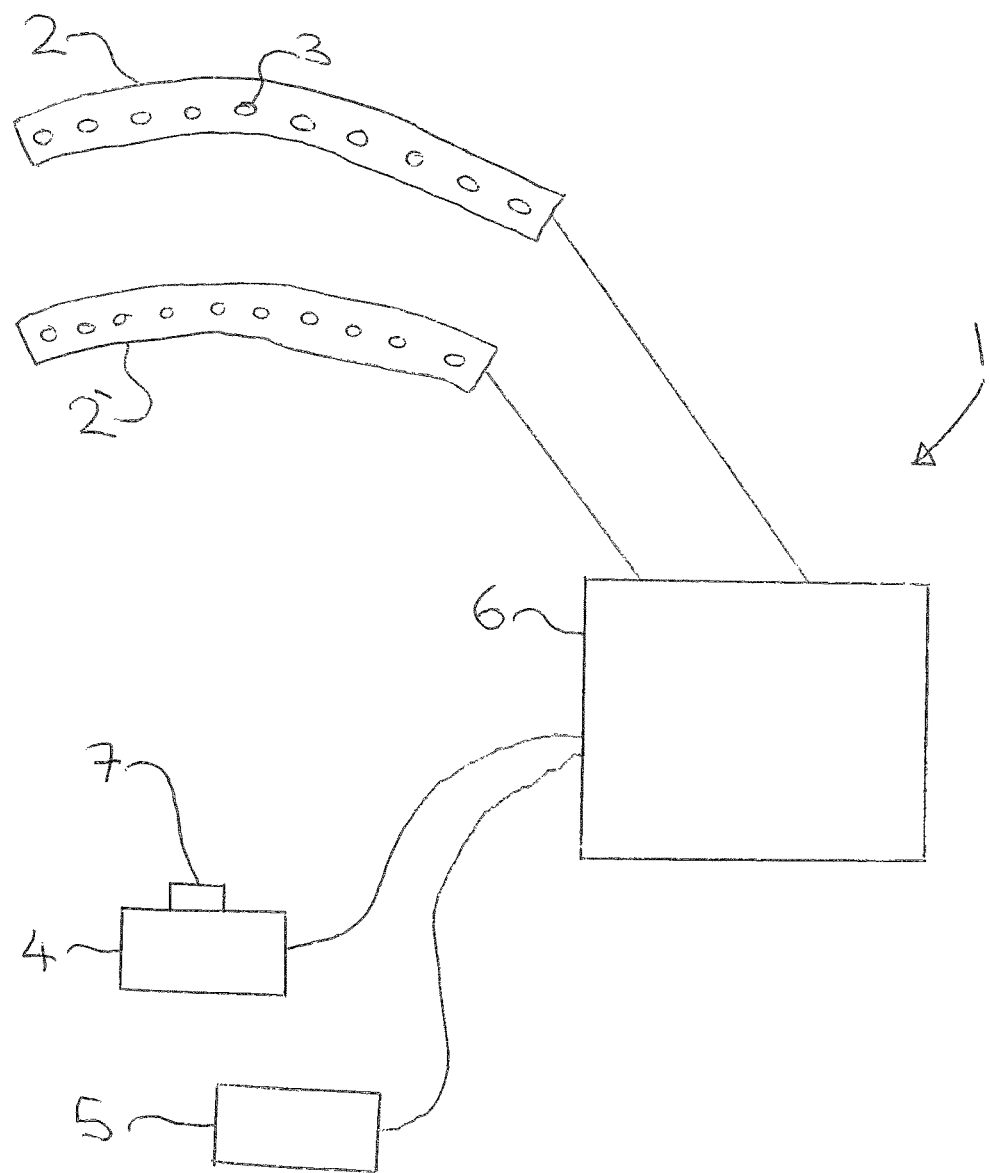
FIG. 1 is a schematic view of apparatus for inducing sleep according to an embodiment of the invention in which the stimulus is light.

FIG. 1 shows an apparatus for inducing sleep according to one embodiment of the present invention. The apparatus 1 includes stimulus means, which in the illustrated embodiment comprises upper and lower displays in the form of elongate tracks 2 and 2'. Each track has plurality of lights 3, for example LEDs, disposed thereon and the upper and lower tracks are vertically separated from each other. The elongate tracks may be curved.

The tracks 2, 2' are mounted on support arms connected to a base unit 6. The base unit 6 may take the size and form of a typical bedside clock radio unit and is intended to be normally located on a bedside table or the like so that it is readily accessible for use every night. Alternatively, the base unit 6 may be incorporated into the headboard of a bed or provided as a wall or ceiling unit, mountable above or near the bed. Other alternatives may be envisaged. The tracks and support arms are preferably pivotally connectable to the base unit 6 so that the tracks are selectively positionable into a field of view of the subject once the subject is laying down in bed and can be pivoted up and out of the way (over or into the base unit) when not required. Preferably the tracks are orientated generally horizontally when in the field of view of the subject.

The apparatus further comprises input means 4 for measuring an active (conscious) input provided by the subject and monitoring means 5 for measuring a physiological characteristic of the subject. Processing means comprising control hardware and software (not shown) may conveniently be disposed within the base unit 6. Both input means 4 and monitoring means 5 are also connected to or are part of the base unit 6.

When the subject is ready to go to sleep, they lay in bed with the tracks above their head in their field of view. The upper display, i.e. track 2 may be positioned so that it is slightly uncomfortable for the subject to view, whereas the lower display, i.e. track 2' may be positioned in an ideally comfortable viewing position. The subject holds the input means 4 in one hand.

The apparatus 1 is configured to provide a subject with a visual stimulus by illuminating at least one of the lights 3 on the elongate track 2 or 2'. The initial stimulus may be the illumination of the leftmost LED on the upper track 2. When the subject sees the initial stimulus, he/she actuates the input means 4 (e.g. by pressing a button) so that the apparatus receives an active input from the user made in response to the visual stimulus.

When the apparatus receives an active input from input means 4 the control hardware is configured to record and process the input to determine at least one characteristic of the input. The control hardware is then configured to calculate and provide a second stimulus to the subject, which stimulus is provided by one of the lights 3 on tracks 2 or 2'. For example, the second stimulus may be the illumination of the second from left LED on the upper track 2. The determination of said second stimulus is at least partially based on the determined characteristic of the initial input.

A second active input provided in response to the second stimulus is then provided by the subject. The second active input is recorded by the control hardware and a characteristic of that input is determined. Subsequent stimuli are then sequentially provided, with the calculation of each subsequent stimulus being based at least partially on the determined characteristics of the inputs made in response to a previous stimulus. "Previous stimulus" means the immediately preceding stimulus and/or earlier stimuli.

For example, a sequence of stimuli might comprise the sequential illumination of LEDs 3 from left to right, one at a time, in a repeated pattern in response to the subject's active inputs. The speed at which the pattern progresses, i.e. the time delay between each stimulus could depend on the subject's speed of response. When the subject is most alert, there may be little time delay between the creation of the stimulus and the subject's active response. As the subject becomes less alert and more sleepy, the subject will respond more slowly. The apparatus can detect this and make appropriate changes to the pattern or timing or other characteristic of the next stimuli to maximise the meditative and/or cognitive effect to encourage sleep.

For example, the brightness of the light stimulus may be decreased, the light stimulus may be provided on the lower of the two curved tracks 2, 2', or a combination of the above changes may be made. Furthermore, a passive input may also be taken from the subject in the form of a monitored physiological characteristic such as respiratory rate, which input may be used to detect how close the subject is to falling asleep. The stimuli provided to the subject may then be calculated based on both the active and the passive input. The passive input may be any one of, or any combination of the subject's heart rate, electrical brain activity, temperature, blood pressure and respiratory rate.

The calculation of the stimuli may determine any one of, or any combination of, the brightness, colour, shape, position, delay time before illumination, the speed of illumination of the lights 3 disposed on tracks 2 and 2', the track on which the light that is illuminated is disposed and the position on the track of the light that is illuminated.

Active input means 4 may be a switch which the subject actuates in response to the stimulus, thus providing an active input. Said switch may be a button 7 disposed on a handheld trigger device wherein the subject presses button 7 in response to the stimulus. The determined characteristic of the input may be one of, or any combination of, the time delay between the stimulus and the input, the speed with which the button 7 is depressed, the pressure applied to the button 7, the length of time for which the button 7 remains pressed, movement or vibration of the input means 4 when the button 7 is pressed and the position of the input means 4 in the subject's hand when the button 7 is pressed.

The determination of the stimuli may additionally be based on a characteristic of a physiological characteristic of the subject recorded by monitoring means 5.

The monitoring means 5 may comprise a band to be placed around the subject's finger, wrist, chest or another suitable part of the subject's body. Alternatively, the monitoring means may be a handheld device.

The monitoring means 5 measures a physiological characteristic of the subject, which may be any one of, or any combination of, the subject's heart rate, electrical brain activity, body temperature, blood pressure and respiratory rate. The monitoring means 5 may continue to measure physiological characteristics of the subject whilst the subject is asleep, which characteristics may include involuntary movement whilst asleep. This data may be usefully used later for conventional sleep analysis.

The apparatus may also include ambient monitoring means (not shown) for recording ambient characteristics of the subject's environment, for example the time, room temperature, light level or sound level.

Optionally the active input means 4, the monitoring means 5 and/or the ambient monitoring means may be formed as a single unit.

It will be readily apparent to the skilled person that the calculation of the stimuli may be performed by conventional control hardware provided with suitable software to calculate the stimuli required in response to a given active input or combination of inputs from the subject (possibly in combination with physiological and/or ambient data). Such control hardware may comprise a processor configured to receive electrical signals from inputs 4 and 5, process the data provided thereby and provide an output signal to lights 3. Software implementing predetermined algorithms may be used to adjust the output provided to lights 3 based on the received inputs and determined characteristics. The software may reduce or increase the length of time between stimuli, the brightness of the lights and the location of the activated lights based on the characteristic of the inputs made in response to the stimuli. In one embodiment the software may provide light stimuli which move horizontally, either from left to right or right to left, across the subject's field of vision, and the delay time between stimuli may be adjusted based on a characteristic of the subject's response. The characteristic of the subject's response may be the delay time between the provision of a stimulus and the provision of an active input in response to the stimulus.

Furthermore, as the subject becomes more tired and the delay time between the provision of the stimuli and the provision of the active inputs in response to the stimuli increases, the software may activate the lights 3 on the lower track 2' rather than the upper track 2. The transition of the stimuli from the upper track 2 (which is relatively uncomfortable to view) to the lower track 2' (whose position is ideally comfortable to view) may in itself have the effect of encouraging the subject to close their eyes.

The software may implement machine learning techniques to optimise the stimuli provided to the subject over time. Such machine learning may comprise detecting when the subject has fallen asleep, recording the pattern of stimuli that were delivered before the subject fell asleep and adjusting future stimuli based on the recorded patterns of stimuli.

The control hardware may conveniently be disposed within the base unit 6, and the inputs and outputs may be received by and sent from the control hardware either via direct electrical connections or wirelessly using conventional wireless communication technology. If wireless communication is employed between the input means 4, 5 and/or the lights 3 then the input means and/or the lights may be physically connected to the base unit 6 for charging when the apparatus is not in use.

In the embodiment shown in FIG. 1 approximately ten LED lights 3 may be provided on tracks 2. Alternatively, the display may comprise one or more screens or other devices capable of displaying light at different locations.

Figure 2:
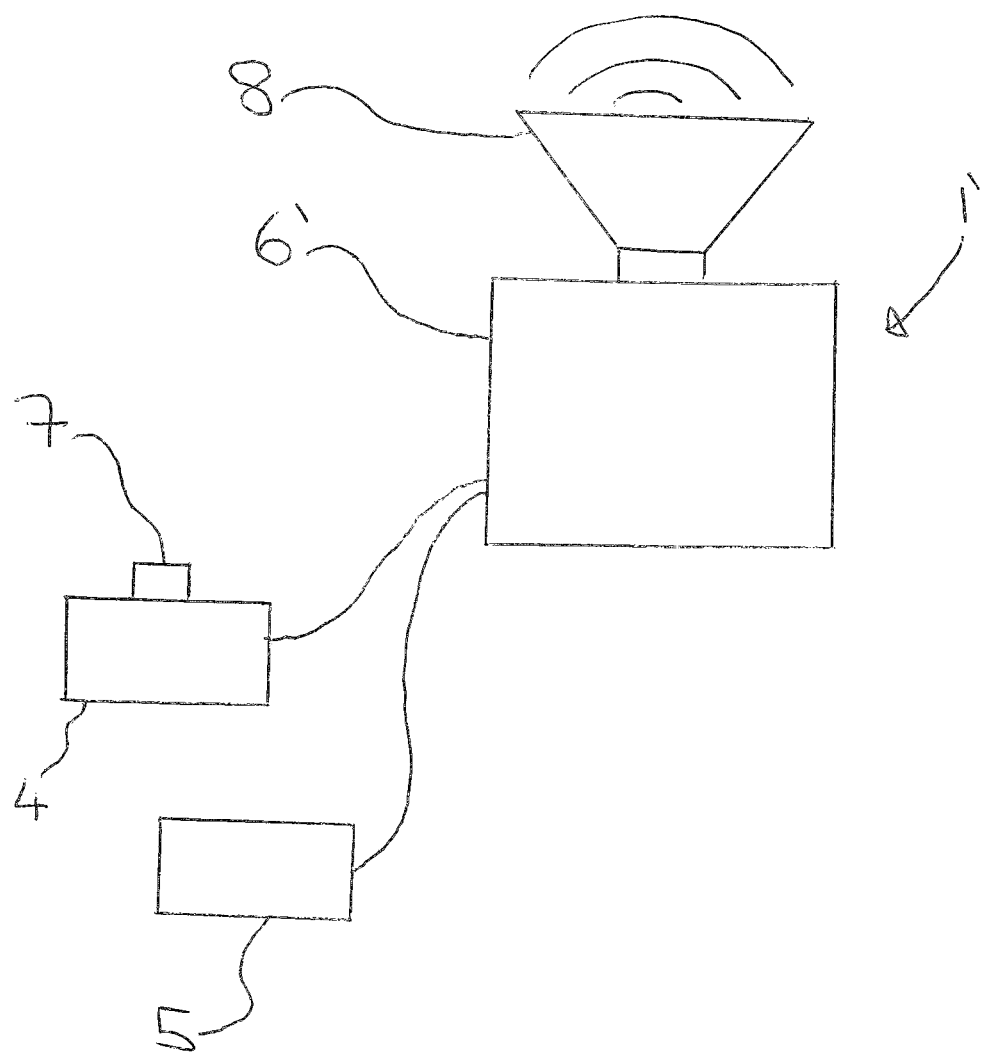
FIG. 2 is a schematic view of apparatus for inducing sleep according to an embodiment of the invention in which the stimulus is sound.

An alternative embodiment in which the stimulus is audible rather than visual is shown in FIG. 2. Apparatus 1' is provided with active input 4 having button 7, monitoring means 5 and a base unit 6 in which control hardware may be disposed. In this embodiment the stimulus means is an audio transducer. In the illustrated embodiment the audio transducer is a loudspeaker 8, which is shown disposed on the base unit 6'. In other embodiments the audio transducer may be headphones or earphones or the like.

In the embodiment shown in FIG. 2 the active input means 4 and monitoring means 5 function in the same manner as described above in relation to FIG. 1. However, in the FIG. 2 embodiment, the lights 3 are replaced with loudspeaker 8, which provides audible stimuli. The stimuli provided by loudspeaker 8 are calculated based on a characteristic of at least one active input provided by the user, and optionally also based on data from the monitoring means 5 and/or ambient monitoring means (not shown).

The calculation of the audible stimulus may comprise adjusting any one of, or any combination of, the volume, pitch or timbre of the stimulus and/or delay time between stimuli.

In another embodiment (not illustrated), a combination of both audible and visual stimuli may be used, for example lights 3 and loudspeaker 8. In this way the apparatus may be operated in an "audible only" mode wherein only the loudspeaker provides stimuli, a "visual only" mode wherein only the lights provide stimuli or a "combined" mode wherein both the lights and the loudspeaker provide stimulus. This embodiment may provide an apparatus suitable for use by people who are either blind or deaf.

The skilled reader will appreciate that stimuli other than sound and light may also be used. For example, a vibration or other tactile stimulus may be provided via a worn wristband or the like.

Although the above apparatus has been described with respect to use in inducing sleep, it will be understood that additional uses are also possible. Such additional uses may include (without limitation), measuring the alertness of a subject, helping to calm an anxious subject, helping a subject to wake up from sleep and a gaming mode. Furthermore, additional functions may conveniently be incorporated into apparatus 1 and 1'. Such additional functions may include (without limitation) an alarm clock, a radio, a SAD light, a docking station for a mobile phone or music player, a CD player, and a measurement device to record the ambient characteristics of the subject's environment, these most likely but not necessarily being located in the base unit 6. The ambient characteristics that the device is configured to measure may include (without limitation) one or more of time, room temperature, light level and sound level.

In a further embodiment, the base unit may have USB/internet ports for additional inputs providing contemporaneous physiological data, for example EEG, that could contribute to the calculation of the stimuli. USB or wireless inputs could also be used to download historic physiological data to the apparatus, for example data from a step counter collected during the previous day, so that the apparatus can take into account the subject's level of daily physical activity when calculating the stimuli.

The base unit may include means to enable a smartphone to plug in directly in order to download such data.

In embodiments having an audio stimulus, the apparatus could be programmed to include an audible or subliminal command to the subject to close their eyes at an appropriate stage (for example as a light stimulus transitions from the upper display to a lower display). Other words or commands, such as those that might typically be used in hypnosis (e.g. "relax", "notice the lights dim", "let your eyelids close" etc) may be incorporated into an audio output.

The apparatus could take the form of an all-in-one bedroom sleep inducing and monitoring tool including, not only the sleep inducing function described above but also more conventional physiological and ambient data collection and analysis capability.

Throughout the description and claims of this specification, the phrase "active input" and variations thereof mean an input which the subject makes a conscious decision to provide, for example the pressing of a button. This is in contrast to passive inputs provided without the subject's conscious decision, for example an input based on a monitored physiological characteristic such as pulse rate or an ambient characteristic such as room temperature.

Throughout the description and claims of this specification the phrase "inducing sleep" means providing stimuli designed to encourage a subject to fall asleep, and is not intended to (and does not) imply that such stimuli must necessarily be successful in causing the subject to fall asleep.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments.

The reader's attention is directed to all papers and documents which are filed concurrently with or previous to this specification in connection with this application and which are open to public inspection with this specification, and the contents of all such papers and documents are incorporated herein by reference.

The invention claimed is:

1. Apparatus for inducing sleep comprising:
    a. stimulus means for providing a subject with a sleep inducing or calming stimulus;
    b. input means for recording an active input provided by the subject in response to the stimulus;
    c. processing means for processing said active input to determine a characteristic of said active input; and
    d. a base unit housing one or more of said means,
    wherein the apparatus is capable of sequentially providing the subject with at least three stimuli, each next stimulus being based on the characteristic determined from the active input made in direct response to a previous one of the at least three stimuli.

2. Apparatus as claimed in claim 1 wherein said stimulus means is a display and said stimulus is light.

3. Apparatus as claimed in claim 2 wherein said display is mounted on said base unit and selectively positionable, in use, into a field of view of a subject.

4. Apparatus as claimed in claim 2 wherein a position and/or brightness and/or a colour and/or a shape of the next stimulus on the display and/or the time interval between stimuli is based on the characteristic of the active input provided in response to a previous one of the at least three stimuli.

5. Apparatus as claimed in claim 2 wherein said display comprises an upper display and a lower display.

6. Apparatus as claimed in claim 5 wherein said upper display and/or said lower display each comprises an elongate track.

7. Apparatus as claimed in claim 6 wherein the elongate tracks of said upper display and/or said lower display are oriented generally horizontally when in the field of view of a subject.

8. Apparatus as claimed in claim 6 wherein each elongate track is mounted on a support arm attached to said base unit, each elongate track being vertically separated from the other.

9. Apparatus as claimed in claim 5 wherein said processing means determines whether said next stimulus should be displayed on the upper or the lower display depending on said characteristic of said active input.

10. Apparatus as claimed in claim 5 wherein at least the first of said stimuli is displayed on said upper display.

11. Apparatus as claimed in claim 2 wherein said stimuli comprise a sequence of lights moving horizontally from left to right across the subject's field of view.

12. Apparatus as claimed in claim 1 wherein said stimulus means is an audio transducer and said stimulus is sound.

13. Apparatus as claimed in claim 12 wherein said audio transducer is a loudspeaker, headphones or earphones.

14. Apparatus as claimed in claim 12 wherein a volume and/or pitch and/or timbre of the next sound stimulus and/or a delay time between sound stimuli is changed based on the characteristic of the active input provided in response to a previous sound stimulus.

15. Apparatus as claimed in claim 1 wherein said active input comprises the actuation of a switch.

16. Apparatus as claimed in claim 15 wherein said characteristic of said active input comprises a time delay between the provision of the stimulus to the subject and the actuation of the switch by the subject.

17. Apparatus as claimed in claim 16 wherein said stimulus means is a display and said stimulus is light, wherein said display comprises an upper display and a lower display, wherein said processing means determines whether said next stimulus should be displayed on the upper or the lower display depending on said characteristic of said active input, and wherein the display of said next stimulus transitions from said upper display to said lower display in response to an increase in said time delay.

18. Apparatus as claimed in claim 1 further comprising monitoring means for recording a physiological characteristic of the subject, wherein said next stimulus is based on the characteristic of said active input and said physiological characteristic.

19. Apparatus as claimed in claim 18 wherein said physiological characteristic is one or more of the subject's heart rate, electrical brain activity, body temperature, blood pressure and respiratory rate.

20. Apparatus as claimed in claim 1 further comprising ambient monitoring means for recording an ambient characteristic of the subject's environment, wherein said next stimulus is based on the characteristic of said active input and said ambient characteristic.

21. Apparatus as claimed in claim 20 wherein said ambient characteristic is one or more of time, temperature, light level and sound level.

22. Apparatus as claimed in claim 1 wherein the determination of said next stimulus is additionally based on a characteristic of at least one active input provided in response to a stimulus provided before the immediately preceding stimulus.

23. Apparatus for inducing sleep comprising:
   a. a stimulator configured to provide a subject with a sleep inducing or calming stimulus;
   b. an input device configured to record an active input provided by the subject in response to the stimulus;
   c. a processor configured to process said active input to determine a characteristic of said active input; and
   d. a base unit housing one or more of said stimulator, input device and processor,
   wherein the apparatus is capable of sequentially providing the subject with at least three stimuli, each next stimulus being based on the characteristic determined from the active input made in direct response to a previous one of the at least three stimuli.

* * * * *